United States Patent [19]

Levy

[11] Patent Number: 4,955,810

[45] Date of Patent: Sep. 11, 1990

[54] DENTIN THICKNESS MONITOR

[76] Inventor: Guy Levy, 49, rue Croix de Regnier, 13004 Marseille, France

[21] Appl. No.: 309,560

[22] Filed: Feb. 13, 1989

[30] Foreign Application Priority Data

Mar. 7, 1988 [FR] France .............................. 88 03089

[51] Int. Cl.$^5$ ............................................. A61C 19/04
[52] U.S. Cl. ..................................... 433/72; 433/114; 433/215
[58] Field of Search ..................... 433/215, 72, 32, 75, 433/27, 114; 33/513, 514

[56] References Cited

U.S. PATENT DOCUMENTS 3,753,434 8/1973 Pike et al. ............................. 433/32
3,901,216 8/1975 Felger .................................... 433/27

FOREIGN PATENT DOCUMENTS 3615632 11/1987 Fed. Rep. of Germany ...... 433/215
2590476 5/1987 France .................................... 433/72

OTHER PUBLICATIONS

"Mesure Électronique de la Longueur des Canaux", *Revue Francaise D'Endodontie*, vol. 3, No. 2, Jun. 1984, pp. 19–40.

Primary Examiner—Cary E. Stone
Attorney, Agent, or Firm—Spensley Horn Jubas and Lubitz

[57] ABSTRACT

A method and apparatus for measuring the thickness of the dentin layer of a tooth in a patient, at a region where the dentin is exposed, during a dental treatment, by the steps of: establishing an electric voltage between the dentin at the region where it is exposed and a region of the patient's body spaced from the tooth to create an electric current flow through body tissue between those regions; monitoring the current flow to produce an indication of the electrical impedance between those regions; and converting the electrical impedance indication into an indication of the thickness of the dentin layer.

14 Claims, 2 Drawing Sheets

DENTIN THICKNESS MONITOR

BACKGROUND OF THE INVENTION

This invention relates to the treatment of dental caries and particularly concerns control of the drilling procedure employed in such treatment.

In many cases, tooth decay extends into the tooth dentin layer, so that a part of that layer must be removed. At the same time, every effort must be made to avoid penetration by the drill bit to the underlying pulp tissue. Heretofore, this has depended entirely on the dentist's skill and judgement.

It has already been proposed to employ resistance measurement to monitor the penetration of an endodontic file to periodontal tissue in connection with root canal therapy. Such a technique is described, for example, in U.S. Pat. No. 3,753,434, which issued to Pike, et al., on Aug. 21, 1973. According to the technique disclosed in this reference, resistance measurements are made while the file is being advanced along a root canal, where it will be in contact with pulp tissue. In the performance of the procedure described in this patent, the tooth dentin is of no concern.

It has also been proposed to monitor the thickness of a tooth dentin layer by measuring the resistance between the upper surface of the dentin layer and a point within the patient's mouth. This is described in FRG-laid-open application 3615632. However, this publication indicates that dentin layers of varying thickness will produce a resistance variation in the range of 10-60 KΩ. However, applicant has found that the resistance of tooth dentin is between one and two orders of magnitude higher than that range of values.

SUMMARY OF THE INVENTION

It is an object of the present invention to provide the dentist with reliable information which will enable complete penetration through the dentin layer to be avoided during treatment of a dental caries.

A more specific object of the invention is to provide a dentist with an indication of the thickness of the dentin layer remaining between the tip of the drill bit and the underlying pulp tissue.

A further object of the invention is to provide a dentist with warning when the tip of the drill bit nears the pulp tissue underlying the dentin layer.

Yet another object of the invention is to provide such information while allowing the dentist to concentrate on the drilling operation.

A further object of the invention is to provide the dentist with a warning if abnormal pulp structures within the dentin layer are encountered.

The above and other objects are achieved, according to the present invention by a method for measuring the thickness of the dentin layer of a tooth in a patient, at a region where the dentin is exposed, comprising: establishing an electric voltage between the dentin at the region where it is exposed and a region of the patient's body spaced from the tooth to create an electric current flow through body tissue between those regions; producing an indication of at least electrical resistance values above 0.5 MΩ between those regions; and converting the electrical resistance indication into an indication of the thickness of the dentin layer.

The objects according to the invention are further achieved by a dental treatment apparatus comprising: dental drill means for drilling a tooth in a patient in order to remove decayed material from the tooth dentin layer; means for applying an electric voltage between the drill means and a region of the patient's body spaced from the tooth to create an electric current flow through body tissue when the drill means are in contact with the tooth dentin; and circuit means connected to the electric voltage applying means for deriving an indication of the thickness of the tooth dentin layer below the drill means as a function of at least electrical resistance values between above 0.5 MΩ between the drill means and the region of the patient's body spaced from the tooth.

DESCRIPTION OF THE PREFERRED EMBODIMENTS

Figure 1:
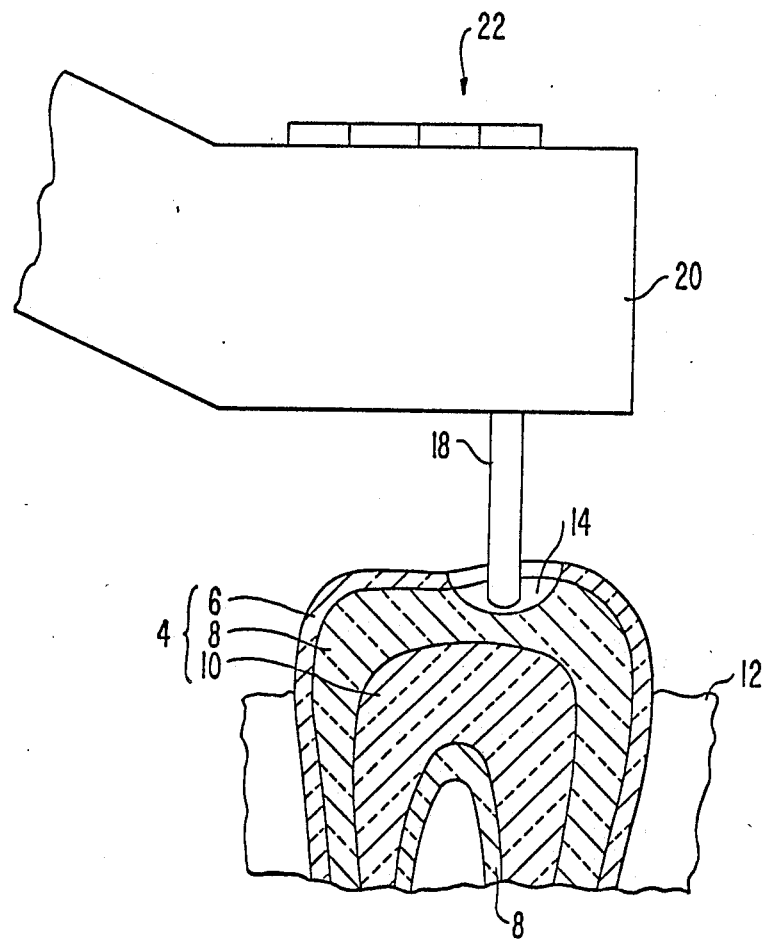
FIG. 1 is a pictorial view showing a dental handpiece engaged in drilling a decayed region of a tooth.

FIG. 1 illustrates a tooth 4 being drilled to remove decayed material (caries) after which the resulting cavity will be filled with a suitable dental material. The tooth 4 is composed of a layer of enamel 6 covering a layer of dentin 8 which, in turn, surrounds a mass of pulp 10. The tooth is surrounded by gum tissue 12.

The decayed region 14 of tooth 4 is removed by means of a dental drill bit 18 supported by a handpiece 20 containing a drive mechanism for rotating drill bit 18. Handpiece 20 carries an array 22 of indicator lights, which may be light emitting diodes (LEDs) which are located to be directly in the dentist's field of view. The purpose of these lights will be described below.

During treatment of a dental caries, it is essential that all decayed material be removed and, to assure that this is accomplished, it is generally necessary to remove a certain amount of healthy material. However, if at all possible, the removal process should stop short of the pulp material 10 because damage to the pulp material can cause subsequent dental problems.

In view of the fact that the dentin layer generally has a small thickness which varies from one tooth to another, it is very difficult for the dentist to know how close the tip of drill bit 18 is to the body of pulp 10.

The present invention is based on the recognition that the resistivity of dentin is substantially higher than that of pulp tissue and other body tissues, so that the electrical resistance between the drill bit and a region of the patient's body spaced from the tooth being treated can be used as a measure of the thickness of the dentin layer remaining between the tip of the drill bit and the dentin/pulp interface.

Specifically, based on tests performed on a number of teeth, the following resistance values have been noted between a drill bit, which is made of conductive material, and an electrode which is being firmly gripped by the patient's hand:

4 mm of dentin between the drill bit tip and the underlying pulp tissue—5 megohms (MΩ)

2 mm of dentin between the drill bit tip and the underlying pulp tissue—2.3 MΩ

1.5 mm of dentin between the drill bit tip and the underlying pulp tissue—2 MΩ

1 mm of dentin between the drill bit tip and the underlying pulp tissue—1.5 MΩ

0 mm of dentin between the drill bit tip and the underlying pulp tissue—0.8 MΩ penetration of the tip of the drill bit into the pulp tissue to a depth of 0.5 mm—0.5 MΩ.

In a practical system, it might be preferable to replace the hand-held electrode with one which is firmly but gently clamped onto the patient's lip. This arrangement would offer the advantage of eliminating resistance variations due to changes in the contact pressure exerted by the patient on the electrode and would be expected to effect a small reduction in the measured resistance level. However, the change in resistance as the tip of the drill bit approaches the dentin/pulp tissue interface would remain at the same level.

Figure 2:
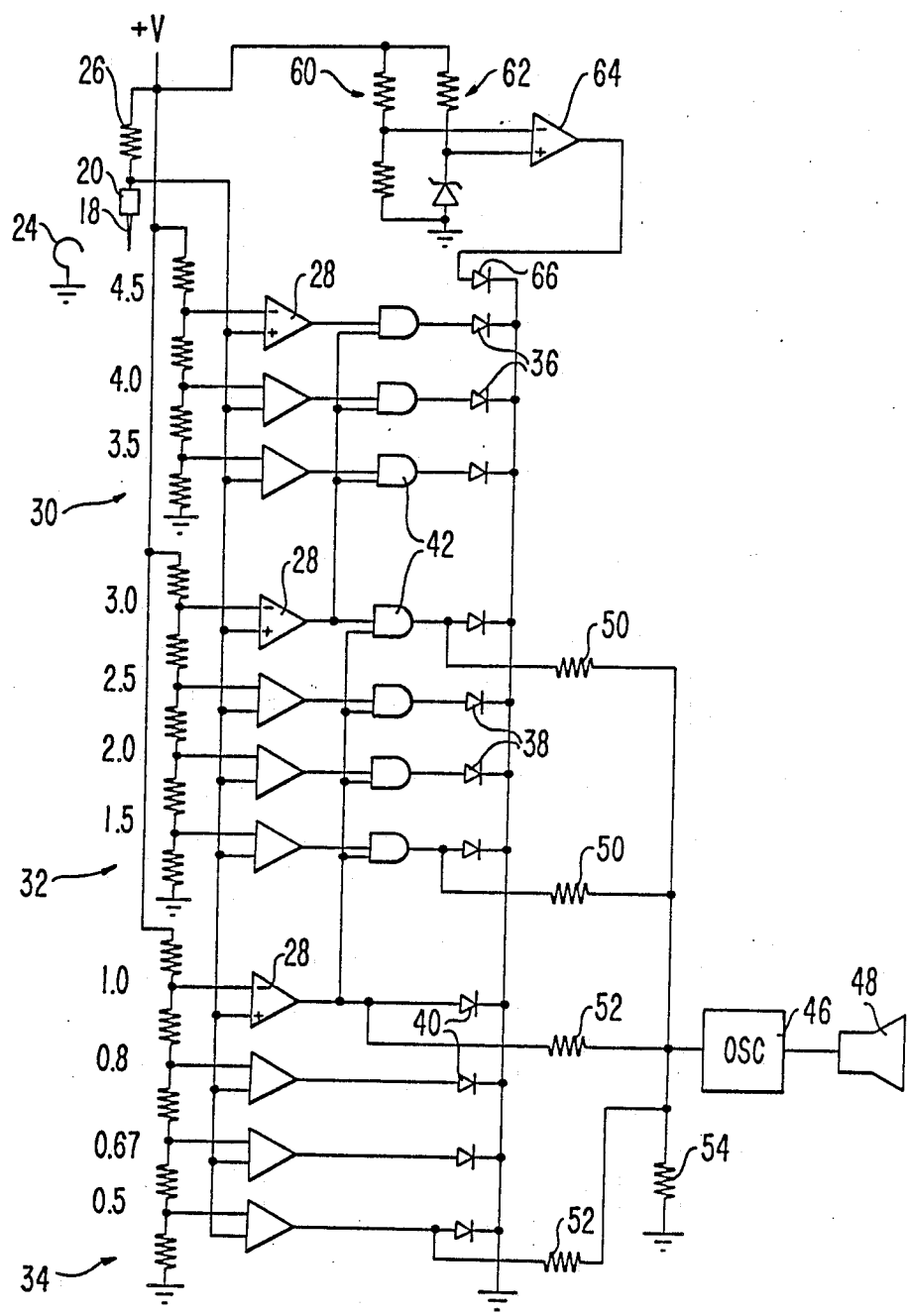
FIG. 2 is a circuit diagram of a preferred embodiment of a system according to the present invention.

One preferred embodiment of a circuit for implementing the present invention is illustrated in FIG. 2 and includes a grounded electrode 24 which is configured to engage the patient's lip. In this circuit arrangement, the handpiece 20, and thus drill bit 18, is connected to a source of positive voltage, +V, so that the resistance between electrode 24 and drill bit 18 can be monitored.

Handpiece 20 is connected to the voltage source via a resistor 26 which forms a voltage divider with the resistance between drill bit 18 and grounded electrode 24, this latter resistance being the resistance which is to be monitored.

Handpiece 20 is additionally connected to the positive inputs of a plurality of comparators 28, each comparator being essentially a high gain differential amplifier. Thus, the voltage applied to the positive input of each comparator 28 is proportional to the value of the resistance which is to be monitored.

The plurality of comparators 28 is divided into three groups, the first group containing three comparators 28, and each of the other two groups containing four comparators 28.

Each comparator group is associated with a respective resistance voltage divider 30, 32, 34, each divider being connected between the source of positive voltage and ground. As will be explained in greater detail below, each group of comparators 28, and the associated voltage divider 30, 32, or 34, is constructed to monitor a selected resistance range. The voltage applied by the voltage dividers to the negative input of each comparator 28 corresponds to the voltage which will be present across the resistance being monitored when that resistance has the value, in megohms, indicated on FIG. 2 to the left of the voltage dividers. Thus, the voltages applied to the negative inputs of the first group of comparators 28 via taps of voltage divider 30 correspond to resistance values between 4.5 and 3.5 MΩ, the voltages applied to the negative inputs of the second group of comparators 28 from taps of voltage divider 32 correspond to resistance values of 3.0–1.5 MΩ, and the voltages applied to the negative inputs of the third group of comparators via taps of voltage divider 34 correspond to resistance values of 1.0–0.5 MΩ.

The output of each comparator 28 is connected to a respective LED, the outputs of the first group of comparators being connected to green LEDs 36, the outputs of the second group of comparators being connectd to yellow LEDs 38 and the outputs of the third group of comparators being connected to red LEDs 40. Each comparator 28 is constructed to produce an output voltage having a polarity which will illuminate the associated LED when the magnitude of the voltage at the positive input of the comparator 28 becomes less than the magnitude of the voltage at the negative input of that LED. Thus, the first green LED 36 will illuminate when the resistance between drill bit 18 and electrode 24 falls below 4.5 MΩ, etc.

The different groups of LEDs are linked by logic circuitry which allows only one group of LEDs to be illuminated at any given time. This logic circuitry includes a plurality of ANDNOT gates 42 each having a direct input connected to the output of a respective comparator 28 in each of the first and second groups and an output connected to the corresponding LED. In addition, each gate 42 has a negating input connected to receive a gating signal. For the second group of comparators, the gating signal is provided from the output of the first comparator of the third group, while for the first group of comparators, the gating signal is provided from the output of the first comparator of the second group.

Assuming that the resistance being monitored decreases from a value of 5 MΩ, the initial decrease from 5 MΩ to 3 MΩ will cause each red LED 36 to be illuminated in turn. When the resistance being monitored falls below 3 MΩ, the output signal from the first comparator 28 of the second group causes the first LED 38 associated with the second group to be illuminated and applies a gate disable signal to the gates 42 associated with the first group. Thus, the green LEDs are extinguished. As the resistance being monitored continues to decrease, successive ones of the yellow LEDs 38 are illuminated.

Then, when the resistance being monitored falls below 1 MΩ, the output signal from the first comparator 28 of the third group illuminates the first red LED 40 and, at the same time, applies a disable signal to each of the gates 42 associated with the second group of comparators so that the yellow LEDs are extinguished. As the resistance continues to drop below 1 MΩ, further red LEDs 40 are illuminated.

Since, with the arrangement, LEDs of only one color are illuminated at a given time, an unambiguous indication of the resistance value range presently being encountered is provided to the dentist.

According to one beneficial feature of the arrangement described thus far, the occurence of an abnormal condition giving rise to a very low resistance value, i.e., below 0.5 MΩ is signaled to the dentist in that all four red LEDs 40 are illuminated simultaneously. It has been found that such a condition can be created, for example, by pulp pockets projecting into the dentin layer.

According to a further feature of the invention, the dentist may be provided with an audible signal corresponding to the illumination of yellow and red LEDs. For this purpose, there is further provided an oscillator 46 connected to drive an audible signal device 48, which may be a type of buzzer. Oscillator 46 is driven by a voltage derived from the illumination signals supplied to LEDs 38 and 40. This voltage is produced by connecting the input of oscillator 46 to the current path of each of those LEDs by respective resistors 50, 52. While one such resistor is associated with each of the yellow and red LEDs, only two of the resistors are shown for each group, in order to simplify the illustration. The input of oscillator 46 is additionally connected to ground via a further resistor 54.

As the number of yellow LEDs 38 which are illuminated increases, the current, and hence the voltage, at the input of oscillator 46 increases, resulting in an increase in the intensity of the signal supplied to audible signaling device 48. A similar result occurs as successive red LEDs 40 are illuminated. Resistors 52 are selected to have lower resistance values than resistors 50 so that the audible signal will have a higher intensity when the red LEDs 40 are being illuminated than when the yellow LEDs 38 are being illuminated.

The illustrated circuit is further provided with a unit which monitors and indicates the supply voltage, +V. This unit includes a resistive voltage divider 60 and a voltage divider 62 composed of a resistor and a zener diode, each voltage divider being connected between the source of positive voltage, +V, and ground. The center tap of resistive voltage divider 60 is supplied to the negative input of a further comparator 64, which, like the other comparators, can be a high gain differential amplifier. The positive input of comparator 64 is connected to the center tap of voltage divider 62 so that the voltage applied to the positived input will correspond to the breakdown voltage of the zener diode, and thus will remain constant until the positive voltage falls to a very low value. The voltage applied to the negative input of comparator 64 varies linearly with +V and the breakdown voltage of the zener diode is selected to be equal to the voltage applied to the negative input of comparator 64 when the supply voltage, +V, drops to an unacceptably low value. The output of comparator 64 is connected to a further green LED 66 in a manner to supply an illuminating signal to LED 66 as long as the positive voltage +V has an accepted value. Thus, if LED should not be lit, the dentist is warned that the power supply, for example a battery, must be replaced or otherwise serviced.

Thus, the arrangement according to the present invention provides the dentist with an easily readable visual indication of the thickness of the dentin layer remaining beneath the drill bit and offers the possibility of supplementing this visual indication with an audible warning signal. In addition, the device according to the present invention provides an immediate indication of the occurrence of an abnormal condition, represented by a resistance value less than 0.5 MΩ, requiring immediate corrective action.

While a direct voltage, +V, will enable the desired monitoring operation to be carried out, a pulsed unipolar voltage will serve to avoid any electrolytic problems which may be caused at the location of electrode 24. If a pulsed unipolar voltage is employed, its frequency is not critical, but a pulse repetition rate of the order of 400 Hz has been found to produce satisfactory results.

Normally, a contact resistance of the order of 7 KΩ will exist between electrode 24 and the patient's body; a resistance of this order of magnitude will not have any noticeable effect on the operation of the circuit.

As shown in FIG. 1, LEDs 22 are preferably mounted directly on handpiece 20, where they will be directly in the field of view of the dentist during the drilling procedure.

This application relates to subject matter disclosed in French Application No. 88 03089 filed on Mar. 7, 1988, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A method for measuring the thickness of the dentin layer of a tooth in a patient, at a region where the dentin is exposed, during a dental treatment, comprising the steps of: establishing an electric voltage between the dentin at the region where it is exposed and a region of the patient's body spaced from the tooth to create an electric current flow through body tissue between those regions; monitoring the current flow to produce an indication of at least electrical resistance values above 0.5 MΩ between those regions; and converting the electrical resistance indication into an indication of the thickness of the dentin layer.

2. A method as defined in claim 1 wherein the electric voltage is a periodically fluctuating unipolar voltage.

3. A method as defined in claims 2 wherein the electric voltage fluctuates at a frequency of at least about 400 Hz.

4. A method as defined in claim 1 wherein the region of the patient's body spaced from the tooth is located at least partially in the patient's mouth.

5. A method as defined in claim 1 wherein said step of monitoring comprises producing an output signal having an amplitude representative of the electrical resistance; and said step of converting comprises producing an indication that the dentin thickness has a first selected value when the output signal reaches a first selected threshold value.

6. A method as defined in claim 5 wherein said step of converting further comprises producing an indication that the dentin thickness has a second selected value when the output signal reaches a second selected threshold value.

7. A method as defined in claim 1 in combination with drilling the tooth to remove decayed material from the dentin layer by means of a dental drill, wherein said step of establishing an electric voltage is carried out by connecting a source of the voltage between the dental drill and an electrode in conductive contact with the region of the patient's body.

8. Dental treatment apparatus comprising: dental drill means for drilling a tooth in a patient in order to remove decayed material from the tooth dentin layer; means connected for applying an electric voltage between said drill means and a region of the patient's body spaced from the tooth to create an electric current which flows through body tissue when said drill means are in contact with the tooth dentin; circuit means connected to said electric voltage applying means for deriving an indication of the thickness of the tooth dentin layer below said drill means as a function of at least electrical resistance values above 0.05 MΩ between said drill means and the region of the patient's body spaced from the tooth.

9. Apparatus as defined in claim 8 wherein said means for applying an electric voltage comprise a circuit for causing the electric current which flows through the patient's body to be a pulsating unidirectional current.

10. Apparatus as defined in claim 9 wherein the current fluctuates at a frequency of greater that about 400 Hz.

11. Apparatus as defined in claim 8 further comprising visual indicator means mounted on said dental drill means and connected to said circuit means for providing a visual indication when the thickness of the dentin layer becomes less than a predetermined value.

12. Apparatus as defined in claim 11 wherein said visual indicator means comprise a plurality of indicator lights each connected to be illuminated when the thickness of the dentin layer becomes less than a respective one of a plurality of predetermined values.

13. Apparatus as defined in claim 12 further comprising audible indicator means connected to said circuit means for providing an audible indication when the thickness of the dentin layer becomes less than a predetermined value.

14. Apparatus as defined in claim 12 wherein said lights are mounted on said drill means to be substantially in the center of the field of view of a person operating said drill means.

* * * * *